(12) United States Patent
Carrington-Smith et al.

(10) Patent No.: US 8,198,476 B2
(45) Date of Patent: Jun. 12, 2012

(54) CARBONYLATION PROCESS FOR THE PRODUCTION OF ACETIC ACID USING METAL-PINCER LIGAND CATALYSTS

(75) Inventors: Emma Louise Carrington-Smith, Berkshire (GB); David John Law, East Yorkshire (GB); Paul Gerard Pringle, Clifton (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 141 days.

(21) Appl. No.: 12/451,755

(22) PCT Filed: May 23, 2008

(86) PCT No.: PCT/GB2008/001776
§ 371 (c)(1), (2), (4) Date: Aug. 25, 2010

(87) PCT Pub. No.: WO2008/145976
PCT Pub. Date: Dec. 4, 2008

(65) Prior Publication Data
US 2010/0324332 A1    Dec. 23, 2010

(30) Foreign Application Priority Data
Jun. 1, 2007 (EP) .................................. 07252240

(51) Int. Cl.
*C07C 51/12* (2006.01)

(52) U.S. Cl. .................................... 562/519; 562/520
(58) Field of Classification Search ................ None
See application file for complete search history.

(56) References Cited

U.S. PATENT DOCUMENTS 7,276,626 B2 * 10/2007 Gaemers et al. ............... 562/519
7,368,597 B2 *  5/2008 Gaemers et al. ............... 562/519

FOREIGN PATENT DOCUMENTS

WO     2004/101487    11/2004
WO     2004/101488    11/2004

OTHER PUBLICATIONS

International Search Report for PCT/GB2008/001776, mailed Aug. 21, 2008.
Written Opinion of the International Searching Authority for PCT/GB2008/001698, mailed Aug. 21, 2008.
Singleton, "The uses of Pincer Complexes in Organic Synthesis", Tetrahedron, Elsevier Science Publishers, Amsterdam, NL, vol. 59, No. 11, Mar. 10, 2003, pp. 1837-1857, XP004413125.

* cited by examiner

*Primary Examiner* — Sudhakar Katakam
(74) *Attorney, Agent, or Firm* — Nixon & Vanderhye

(57) ABSTRACT

A process for the production of acetic acid by the liquid phase carbonylation of an alcohol and/or a reactive derivative thereof in which there is employed a catalyst comprising a complex of rhodium or iridium with a pincer ligand.

14 Claims, No Drawings

CARBONYLATION PROCESS FOR THE PRODUCTION OF ACETIC ACID USING METAL-PINCER LIGAND CATALYSTS

This application is the U.S. national phase of International Application No. PCT/GB2008/001555, filed 23 May 2008, which designated the U.S. and claims priority to European Application No. 07252240.2, filed 1 Jun. 2007, the entire contents of each of which are hereby incorporated by reference.

This invention relates in general to a process for the production of acetic acid by the liquid phase carbonylation of methanol and/or a reactive derivative thereof in the presence of a catalyst comprising a metal-pincer ligand complex.

Preparation of carboxylic acids by rhodium-catalysed carbonylation processes is known and is described, for example, in EP-A-0632006 and U.S. Pat. No. 4,670,570.

EP-A-0632006 discloses a process for the liquid phase carbonylation of methanol or a reactive derivative thereof which process comprises contacting carbon monoxide with a liquid reaction composition comprising methanol or a reactive derivative thereof, a halogen promoter and a rhodium catalyst system comprising a rhodium component and a bidentate phosphorus-sulphur ligand, the ligand comprising a phosphorus dative centre linked to a sulphur dative or anionic centre by a substantially unreactive backbone structure comprising two connecting carbon atoms or a connecting carbon and a connecting phosphorus atom.

Preparation of carboxylic acids by iridium-catalysed carbonylation processes is known and is described, for example in EP-A-0786447, EP-A0643034 and EP-A-0752406.

EP-A-0643034 describes a process for the production of acetic acid by carbonylation of methanol or a reactive derivative thereof which process comprises contacting methanol or a reactive derivative thereof with carbon monoxide in a liquid reaction composition in a carbonylation reactor characterised in that the liquid composition comprises (a) acetic acid, (b) an iridium catalyst, (c) methyl iodide, (d) at least a finite quantity of water, (e) methyl acetate and (f) as promoter, at least one of ruthenium and osmium.

The use of bidentate chelating phosphorus or arsenic ligands in carbonylation processes is known, for example, from GB 2,336,154, U.S. Pat. Nos. 4,102,920 and 4,102,921.

GB 2,336,154 describes a process for the liquid-phase carbonylation of an alcohol and/or a reactive derivative thereof to produce a carboxylic acid in the presence of a bidentate ligand of formula $R^1R^2X—Z—YR^5R^6$, wherein X and Y are independently N, P, As, Sb or Bi, and Z is a divalent linking group.

U.S. Pat. No. 4,102,920 describes a process for the carbonylation of alcohols, esters, ethers and organo halides in the presence of a rhodium complex with a polydentate phosphine or arsenic chelating ligand. U.S. Pat. No. 4,102,921 describes a similar process in the presence of an iridium complex with a polydentate phosphine or arsenic chelating ligand.

WO 2004/101488 describes a process for the liquid phase carbonylation of an alcohol and/or reactive derivative thereof in the presence of hydrogen and a catalyst comprising cobalt or rhodium or iridium co-ordinated with a tridentate ligand.

WO 2004/101487 describes a process for the liquid phase carbonylation of an alcohol and/or reactive derivative thereof in the presence of a catalyst comprising rhodium or iridium co-ordinated with a polydentate ligand wherein the ligand has a bite angle of 145° or is co-ordinated to the metal in a rigid structural conformation.

It has now been found that methanol and/or reactive derivatives thereof may be carbonylated in the liquid phase with carbon monoxide in the presence of a catalyst comprising a metal selected from rhodium and iridium and wherein the metal is complexed to a pincer ligand.

Accordingly, the present invention provides a process for the production of acetic acid by carbonylating methanol and/or a reactive derivative thereof with carbon monoxide in the presence of a catalyst in a liquid reaction composition comprising methyl iodide and a finite concentration of water and wherein the catalyst comprises a complex of a metal with a pincer ligand of general formula (I)

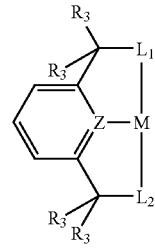

Formula (I)

wherein Z is carbon and $L_1$ and $L_2$ are each a co-ordinating group containing a P-donor atom or a N-donor atom; each $R_3$ is independently selected from hydrogen or a $C_1$-$C_6$ alkyl group and M is selected from Rh and Ir.
or general formula (II)

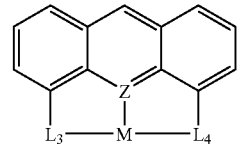

Formula (II)

wherein Z is carbon and $L_3$ and $L_4$ are each a co-ordinating group containing a P-donor atom or a N-donor atom and M is selected from Rh and Ir.

Pincer ligands are a type of chelating ligand. A pincer ligand complexes to a metal via a sigma bond and at least two dative bonds. In the complexes used in the present process, the dative bonds arise from the interaction of a co-ordinating group containing a phosphorous donor atom and/or a group containing a nitrogen donor atom. The pincer ligand comprises two coordinating groups which, independently, contain P, or N, as the donor atom (coordinating atom) in the two co-ordinating groups. The two coordinating groups are represented in formula (I) above as $L_1$ and $L_2$ and represented in formula (II) by $L_3$ and $L_4$. In formulas I and II above, the metal-sigma bond arises from the interaction of the metal and the Z atom. Z is carbon.

The co-ordinating groups, $L_1$, $L_2$, $L_3$ and $L_4$ may each contain phosphorus as the coordinating atom. Such phosphorus-containing groups preferably have general formula $R^1R^2P$ wherein each $R^1$ and $R^2$ is independently selected from $C_1$-$C_6$ alkyl, $C_5$-$C_6$ cycloalkyl and optionally substituted aryl groups, especially phenyl groups. Suitably, each of $R^1$ and $R^2$ is independently a $C_1$-$C_6$ alkyl or an optionally substituted aryl.

Where $R^1$ and/or $R^2$ is a $C_1$-$C_6$ alkyl, the $C_1$-$C_6$ alkyl may be a straight chain or a branched alkyl. Suitably, the $C_1$-$C_6$ alkyl is a methyl, ethyl, iso-propyl, or t-butyl group.

Suitably, $R^1$ and $R^2$ are the same. Thus, each of $L_1$, $L_2$, $L_3$ and $L_4$ independently may be selected from $PMe_2$, $PEt_2$, $P^iPr_2$ and $P^tBu_2$.

Where $R^1$ and/or $R^2$ is an optionally substituted aryl group, the aryl group is preferably an optionally substituted phenyl group. Suitably; $R^1$ and $R^2$ may be $PPh_2$ Preferably, the aryl group is substituted. Each aryl group may be substituted by 1 to 3 substituents. Suitable substituents include $C_1$-$C_6$ alkyl groups such as methyl and iso-propyl groups and $C_1$-$C_6$ ethers such as methoxy groups. Specific examples of substituted aryl groups are mesityl (2,4,6 trimethyl benzene), 2,6 di-isopropyl benzene and ortho anisyl (2-methoxy benzene).

Alternatively, $R^1$ and $R^2$ and the P atom may together form a ring structure having 5 to 10 carbon atoms, such as 9-phosphacyclo[3.3.1]nonane.

Alternatively, the co-ordinating groups, $L_1$, $L_2$, $L_3$ and $L_4$ may each have nitrogen as the coordinating atom. Such nitrogen-containing groups preferably have general formula $R^1R^2N$ wherein $R^1$ and $R^2$ are as defined for $R^1R^2P$ above.

The co-ordinating groups $L_1$ and $L_2$ may be the same or different. For example both $L_1$ and $L_2$ may be the same or different phosphine groups. The co-ordinating groups $L_3$ and $L_4$ may be the same or different, but are preferably the same.

Each $R_3$ is independently selected from hydrogen and a $C_1$-$C_6$ alkyl group. The $C_1$-$C_6$ alkyl group may be a straight chain or a branched chain alkyl. For example, $R_3$ may be methyl, ethyl, isopropyl. Each $R_3$ may be the same or different. Suitably, each $R_3$ is hydrogen.

Z in formulas (I) and (H) is carbon, thus the backbone ring structure is, in formula (I) a benzene ring and, in formula (II), an anthracene ring. The benzene and anthracene backbone rings may be substituted by 1 or more substituents. Suitable substituents may be $C_1$-$C_6$ alkyl, $C_1$-$C_6$ ethers, halide and nitro groups. Preferred substituents are $C_1$-$C_6$ ethers, such as methoxy, and nitro groups.

Suitable pincer ligand metal complexes include those of structures 1 to 4 below, wherein M is a metal selected from rhodium and iridium.

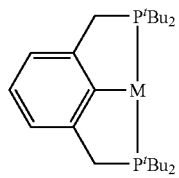

Structure (1)

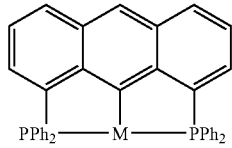

Structure (2)

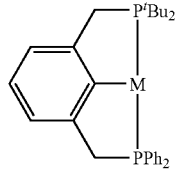

Structure (3)

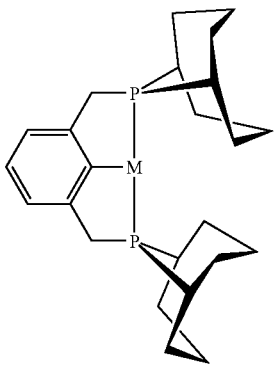

Structure (4)

Suitably, in structures (1) and (2), M is Rh or Ir and in structures (3) and (4), M is Ir.

For use as catalysts in the carbonylation of methanol and/or reactive derivatives, the pincer ligands of formulas (I) and (II) are complexed to one of iridium and rhodium. Suitably, pincer ligands of formula (I) are complexed with rhodium and pincer ligands of formula (II) are complexed with iridium.

Pincer ligands are available commercially or may be synthesised according to methods known in the art. More specifically, the pincer ligands may be synthesised according to methods as described or analogous to those described by C. J Moulton and B. L Shaw, J. Chem. Soc., Dalton Trans. 1976, 1020-1024 and M. W. Haenel, S. Oevers, J. Bruckmann, J. Kuhnigk and C. Krüger, *Synlett.*, 1998, 301, the contents of which are herein incorporated by reference.

Pincer ligands of Formula (I) wherein the $L_1$ and $L_2$ groups are desired to be the same, may be prepared, for example, by treating α,α'-dibromoxylene with 2 equivalents of a secondary phosphine or a secondary amine in a polar solvent such as acetonitrile. The resulting diphosphonium or diammonium salt is then deprotonised with an aqueous base such as sodium acetate in water to give the pincer ligand. Where it is desired to prepare pincer ligands of Formula (I) but wherein the $L_1$ and $L_2$ groups are different, the pincer ligand may be prepared, for example, by treating α,α'-dibromoxylene with 1 equivalent of a secondary phosphine or a secondary amine in a non-polar solvent such as toluene. The resulting monophosphonium or monoammonium salt is then dissolved in a polar solvent such as acetonitrile and treated with 1 equivalent of a different secondary phosphine or secondary amine. The resulting phosphonium or ammonium salt is then deprotonised with an aqueous base such as sodium acetate in water to give the desired pincer ligand.

Pincer ligands of Formula (II) can be made from 1,8-dihaloanthracenes such as 1,8-difluoroanthracene which itself can be prepared by substitution/reduction of 1,8-dichloroanthroquinone. Pincer ligands of Formula (II) wherein the $L_1$ and $L_2$ groups are the same (both $PR^1R^2$ or $NR^1R^2$) can be made by treatment of 1,8-dihaloanthracenes with 2 equivalents of $KPR^1R^2$ (prepared from $HPR^1R^2$ and a base such as KH) or 2 equivalents of a secondary amine $HNR^1R^2$ in a solvent such as toluene in the presence of a Buchwald-Hartwig amination palladium catalyst and a base such as $Na_2CO_3$. Pincer ligands of Formula (II) wherein $L_1$ and $L_2$ are different can be made by treatment of 1,8-dihaloanthracenes with 1 equivalent of $KPR^1R^2$ or 1 equivalent of secondary amine $HNR^1R^2$ in a solvent such as toluene in the presence of a Buchwald-Hartwig amination palladium catalyst and a base such as $Na_2CO_3$. The resulting 1-phosphino-8-haloanthracene or 1-amino-8-haloanthracene monoamine is then treated with 1 equivalent of a different KPR$^1$R$^2$ or a different secondary amine HNR$^1$R$^2$ t in a solvent such as toluene in the presence of a Buchwald-Hartwig amination palladium catalyst and a base such as Na$_2$CO$_3$ to give the desired pincer ligand.

The catalyst is added to the liquid reaction composition in the form of a pre-formed metal-pincer ligand complex. The pre-formed metal-pincer ligand complex may be prepared, for example, by heating a mixture of a suitable iridium- or rhodium-containing compound with the pincer ligand in a solvent such as 2-methoxyethanol followed by removal of the solvent under reduced pressure.

Suitable iridium-containing compounds include IrCl$_3$ and [Ir$_2$Cl$_2$(cyclooctadiene)$_2$].

Suitable rhodium-containing compounds include RhCl$_3$.3H$_2$O, [Rh$_2$Cl$_2$(CO)$_4$], and [Rh$_2$Cl$_2$(cyclooctadiene)$_2$].

Preferably, the metal-pincer ligand complex is soluble in the carbonylation reaction solvent, for example, acetic acid, at the carbonylation reaction temperature.

In the carbonylation of methanol to produce acetic acid, the presence of hydrogen is known to result in the formation of undesirable liquid by-products such as acetaldehyde, ethanol and propionic acid. Propionic acid requires an expensive and energy intensive distillation column to separate it from the acetic acid product. Furthermore acetaldehyde can undergo a series of condensation and other reactions to yield, eventually, higher organic iodide compounds. Some of these materials, especially, for example, hexyl iodide, are difficult to remove by conventional distillation and further treatment steps are sometimes necessary to give acetic acid of sufficient purity. EP-A-0 849 251, which describes an iridium catalysed process for the carbonylation of methanol to acetic acid, states that the amount of hydrogen in the carbon monoxide feed is preferably less than 1 mol % and the hydrogen partial pressure in the reactor is preferably less than 1 bar. Similarly, EP-A-0 728 727, which describes a rhodium catalysed process for the carbonylation of methanol to acetic acid, states that the hydrogen partial pressure in the reactor is preferably less than 2 bar.

It has also been found that, using certain rhodium catalysts for methanol carbonylation, the presence of hydrogen in the carbon monoxide feed leads to the production of ethanol and acetaldehyde with only minor amounts of acetic acid being produced.

U.S. Pat. No. 4,727,200, for example, describes a process for the homologation of an alcohol by reaction with synthesis gas using a rhodium-containing catalyst system. The major product formed with a synthesis gas feed is ethanol, acetic acid being a relatively minor by-product.

It has now been found that, in the carbonylation of methanol and/or reactive derivatives thereof with carbon monoxide and in the presence of hydrogen, use of the metal-pincer ligand complexes results in improved selectivity to carboxylic acid products and reduced selectivity to by-products such as propionic acid. Thus high selectivity to the desired acetic acid can be achieved in the presence of hydrogen, allowing carbon monoxide feed streams with higher contents of hydrogen to be employed in the carbonylation process. This has significant cost savings. In particular, utilising a carbon monoxide feed with 1 mol % hydrogen up to 5 mol % hydrogen allows less expensive, non-cryogenic, methods of syngas separation to be employed, such as membrane separation technologies.

Preferably, the concentration of the metal-pincer ligand catalyst complex in the liquid reaction composition is in the range 500 to 2000 ppm.

The liquid reaction composition comprises methyl iodide. The concentration of methyl iodide in the liquid reaction composition is suitably in the range from 1 to 30% by weight, for example from 1 to 20% by weight.

Suitable reactive derivatives of methanol include methyl acetate, methyl iodide and/or dimethyl ether.

The liquid reaction composition comprises a finite concentration of water. By finite concentration of water, as used herein, meant that the liquid reaction composition comprises at least 0.1 wt % water. Preferably, water may be present at a concentration in the range from 0.1 to 30%, for example from 1 to 15%, and more preferably from 1 to 10%, by weight based on the total weight of the liquid reaction composition.

The water may be introduced to the carbonylation reactor together with or separately from the carbonylatable reactants. Water may be separated from the liquid reaction composition withdrawn from the reactor and recycled in controlled amounts to maintain the required concentration in the liquid reaction composition.

Acetic acid may be present in the liquid reaction composition as solvent.

The carbon monoxide for use in the present invention (when fed separately to any hydrogen feed) may be essentially pure or may contain inert impurities such as carbon dioxide, methane, nitrogen, noble gases, water and C$_1$ to C$_4$ paraffinic hydrocarbons.

The partial pressure of carbon monoxide in the reactor may suitably be in the range from 1 to 70 barg.

Hydrogen may be fed to the reactor separately from the carbon monoxide feed, but is preferably fed to the reactor as a mixture with carbon monoxide. Preferably, a mixture of carbon monoxide and hydrogen is obtained from a commercial source such as from the reforming of hydrocarbons. The commercial reforming of hydrocarbons produces a mixture of CO, hydrogen and CO$_2$, such mixture being generally referred to as syngas. Syngas typically comprises a mol ratio of hydrogen to CO in the range 1.5:1 to 5:1.

The hydrogen to carbon monoxide mole ratio in the feed is suitably between 1:100 and 10:1, such as 1:20 to 5:1.

The hydrogen partial pressure in the reactor is suitably in the range 0.1 barg to 20 barg, such as 2 bar to 20 barg, for example, 0.1 to 10 barg, such as 0.1 to 5 barg.

The carbonylation reaction may be carried out at a total pressure in the range from 10 to 100 barg. The temperature may suitably be in the range from 50 to 250° C., typically from 120 to 200° C.

The process may be operated batchwise or continuously, preferably continuously.

The acetic product may be recovered from the liquid reaction composition by withdrawing vapour and/or liquid from the carbonylation reactor and recovering the acetic acid from the withdrawn material. Preferably, carboxylic acid is recovered from the liquid reaction composition by continuously withdrawing liquid reaction composition from the carbonylation reactor and recovering acetic acid from the withdrawn liquid reaction composition by one or more flash and/or fractional distillation stages in which the acid is separated from the other components of the liquid reaction composition such as the rhodium or iridium or cobalt containing catalyst, methyl iodide, unreacted methanol and water which may be recycled to the reactor.

The invention will now be illustrated by way of example only and with reference to the following examples:

EXAMPLES

Catalyst Preparation
Preparation of cyclorhodate(III) of α,α'-bis(di-t-butylphosphino)-m-xylene (Catalyst A)

Diphosphine (α,α'-bis(di-t-butylphosphino)-m-xylene) (1.00 g, 2.53 mmol), RhCl$_3$.3H$_2$O (0.448 g, 1.69 mmol), H$_2$O (1 cm$^3$) and propan-2-ol (6.5 cm$^3$) were heated under reflux for 42 h, then cooled to −5° C. The product was then filtered and the solvent was removed under reduced pressure to give an orange solid (0.81 g, 1.52 mmol, 60%) of structure:

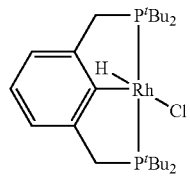

Preparation of cyclorhodate(I) of 1,8-bis(diphenylphosphino)-9-anthryl (Catalyst B)

Diphosphine (1,8-bis(diphenylphosphino)anthracene) (0.2 g, 0.37 mmol), [Rh$_2$Cl$_2$(CO)$_4$] (0.072 g, 0.18 mmol) and toluene (10 cm$^3$) were heated at 60° C. for 19 h to give a red precipitate and orange filtrate (product). The filtrate was separated from the precipitate and the toluene solvent was removed under reduced pressure to give a bright orange solid (1.12 g, 0.18 mmol, 63%) of structure

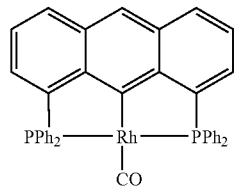

Preparation of cycloiridate(III) of α,α'-bis(di-t-butylphosphino)-m-xylene (Catalyst C)

Diphosphine (α,α'-bis(di-t-butylphosphino)-m-xylene) (1 g, 2.53 mmol), IrCl$_3$.3H$_2$O (0.446 g, 1.27 mmol), H$_2$O (1 cm$^3$) and propan-2-ol (7 cm$^3$) were heated under reflux for 42 h, then cooled to −5° C. Light petroleum (b.p 60-80° C.) was then added to the reaction mixture to give a brown precipitate and red filtrate (product). The filtrate was separated from the precipitate and the solvent was removed under reduced pressure to give a dark brown solid (0.79 g, 1.26 mmol, 50%) of structure:

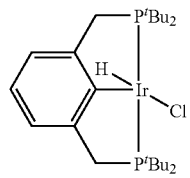

Preparation of cycloiridate(III) of 1,8-bis(diphenylphosphino)-9-anthryl (Catalyst D)

Diphosphine (1,8-bis(diphenylphosphino)anthracene) (0.2 g, 0.37 mmol), [Ir$_2$Cl$_2$(cyclooctene)$_4$] (0.16 g, 0.18 mmol) and 2-methoxyethanol (10 cm$^3$) were heated under reflux for 17 h. The solvent was then removed under reduced pressure to give a red solid (0.193 g, 0.25 mmol, 68% of structure:

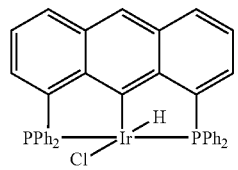

Preparation of cycloiridate(III) of (di-t-butylphosphino)(diphenylphosphino)-m-xylene (Catalyst E)

Diphosphine (di-t-butylphosphino)(diphenylphosphino)-m-xylene (0.1 g, 0.23 mmol), [Ir$_2$Cl$_2$(cyclooctene)$_4$] (0.1 g, 0.12 mmol) in 2-methoxyethanol (8 cm$^3$) were heated under reflux for 2 days. The solvent was then removed under reduced pressure to give a brown solid (0.13 g, 0.2 mmol, 86%) of structure:

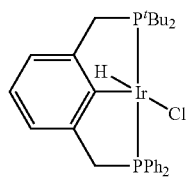

Preparation of cycloiridate(III) of α,α'-bis(9-phosphabicyclo[3.3.1]nonane)-m-xylene (Catalyst F)

Diphosphine (α,α'-bis(9-phosphabicyclo[3.3.1]nonane)-m-xylene) (0.1 g, 0.26 mmol), [Ir$_2$Cl$_2$(cyclooctene)$_4$] (0.12 g, 0.13 mmol) and 2-methoxyethanol (4 cm$^3$) were heated under reflux for 2 h. The solvent was then removed under reduced pressure to give a brown solid (0.1 g, 0.16 mmol, 63%) of structure:

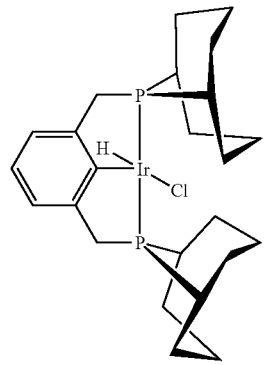

Carbonylation Reactions with Carbon Monoxide

All experiments were carried out in a 100 cm$^3$ hastelloy (Baskerville) autoclave. The autoclave was fitted with a ballast vessel, overhead mechanical stirrer and a catalyst injection facility. Nitrogen was allowed to pass through the apparatus to ensure the autoclave was under anaerobic conditions. The catalysts were preformed prior to use. 0.064 mmol of each of catalysts A to F was weighed out in a glove box and then in a round bottom flask under nitrogen the catalyst was dissolved in methyl acetate (16.1 cm$^3$, 203 mmol), water (3.5 cm$^3$, 194 mmol) and acetic acid (26.2 cm$^3$, 458 mmol). This reaction solution was injected into the reaction vessel under anaerobic conditions. The autoclave was then pressurised with carbon monoxide to ca. 10 bar and heated with stirring to 190° C. Once stable at this temperature, MeI (1.75 cm$^3$, 28.1 mmol) was injected into the autoclave using an overpressure of carbon monoxide. After injection of the MeI, carbon monoxide was fed from the ballast vessel to give an overall pressure of 28 bar. The autoclave pressure was kept constant (±0.5 bar) using carbon monoxide fed from the ballast vessel. The reaction was allowed to continue for 90 min and then the autoclave was allowed to cool to room temperature (over a 3 h period). Once cooled, the autoclave was slowly depressurised. The reaction vessel was removed, then bunged and nitrogen was purged into this vessel. The reaction solution contents were syringed out and syringed to a round bottom flask under nitrogen for analysis. Analysis of the liquid reaction products was carried out by gas chromatography and showed that acetic acid was produced. The results of the experiments are given in Table 1.

TABLE 1

| Catalyst | Conversion to Acetic Acid (%) | CO uptake (bar)* | Rate (CO uptake/Time) (bar/min) |
|---|---|---|---|
| A | 41 | 16 | 0.21 |
| B | 48 | 9 | 0.09 |
| C | 33 | 11 | 0.12 |
| D | 68 | 15 | 0.20 |
| E | 46 | 13 | 0.16 |
| F | 43 | 9 | 0.10 |

*The CO uptake is after 90 min

Carbonylation with Carbon Monoxide in the Presence of Hydrogen

Carbonylation experiments using Catalysts A and D were carried out as for the carbonylation with carbon monoxide described above, except that the carbon monoxide was replaced by a 1:1 mixture of carbon monoxide and hydrogen. The by-product results are shown in Table 2.

TABLE 2

| | Catalyst | | | |
|---|---|---|---|---|
| Feed gas | A CO | A CO/H$_2$ | D CO | D CO/H$_2$ |
| Methyl propionate(ppm) | 70 | 100 | 105 | 75 |
| Propionic acid (ppm) | 555 | 445 | 455 | 490 |
| Total (ppm) | 625 | 545 | 560 | 565 |

As can be seen from Table 2, the presence of hydrogen in the carbonylation process of the present invention, makes no significant difference to the overall propionic by-product make.

The invention claimed is:

1. A process for the production of acetic acid by carbonylating methanol and/or a reactive derivative thereof selected from methyl acetate, methyl iodide, dimethyl ether and mixtures thereof, with carbon monoxide in the presence of a catalyst in a liquid reaction composition comprising methyl iodide and a concentration of water in the range 0.1 to 30% by weight and wherein the catalyst comprises a complex of a metal with a pincer ligand of general formula (I)

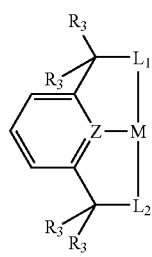

Formula (I)

wherein Z is carbon and $L_1$ and $L_2$ are each a co-ordinating group containing a P donar atom or a N-donor atom; each $R_3$ is independently selected from hydrogen or a $C_1$-$C_6$ alkyl group and M is selected from Rh and Ir, or general formula (II)

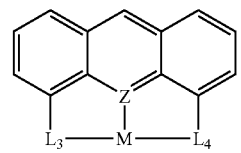

Formula (II)

wherein Z is carbon and $L_3$ and $L_4$ are each a co-ordinating group containing a P donar atom or a N-donor atom and M is selected from Rh and Ir.

2. A process according to claim 1 wherein each of $L_1$, $L_2$, $L_3$ and $L_4$ have the formula $R^1R^2P$ or $R^1R^2N$ wherein each $R^1$ and $R^2$ is independently selected from $C_1$-$C_6$ alkyl, $C_5$-$C_6$ cycloalkyl and optionally substituted aryl group.

3. A process according to claim 2 wherein the optionally substituted aryl group is an unsubstituted phenyl group.

4. A process according to claim 2 wherein each of $L_1$, $L_2$, $L_3$ and $L_4$ are independently selected from PPh$_2$, PMe$_2$, PEt$_2$, P$^i$Pr$_2$ and P$_t$Bu$_2$.

5. A process according to claim 2 wherein $R^1R^2$ and P together form a ring structure having 5 to 10 carbon atoms.

6. A process according to claim 1 wherein each $R_3$ is independently selected from hydrogen, methyl, ethyl or iso-propyl.

7. A process according to claim 1 wherein the backbone ring structure in Formula (I) or Formula (II) is substituted by 1 or more substituents.

8. A process according to claim 1 wherein the metal-pincer ligand complex is selected from

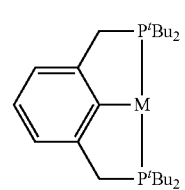

Structure (1)

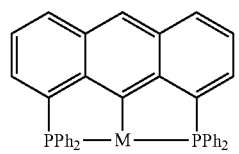

Structure (2)

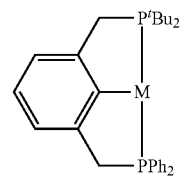

Structure (3)

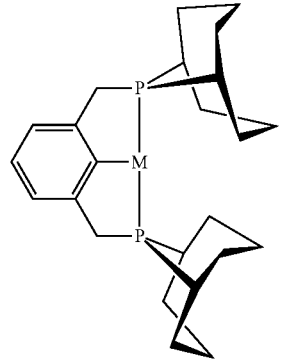

Structure (4)

wherein in each of Structures (1) to (4), M is selected from rhodium or iridium.

9. A process according to claim 1 wherein the metal-pincer ligand complex is present in the liquid reaction composition at a concentration in the range of 500 to 2000 ppm.

10. A process according to claim 1 wherein methyl iodide is present in the liquid reaction composition at a concentration in the range of 1 to 30% by weight.

11. A process according to claim 1 wherein hydrogen is present in the process.

12. A process according to claim 1 wherein the process is carried out at a total reaction pressure in the range 10 to 100 barg.

13. A process according to claim 1 wherein the process is carried out at a temperature in the range 50 to 250 ° C.

14. A process according to claim 1 wherein the reactive derivative is selected from methyl acetate and dimethyl ether.

* * * * *